US005746996A

United States Patent [19]
Govindan et al.

[11] Patent Number: 5,746,996
[45] Date of Patent: May 5, 1998

[54] THIOLATION OF PEPTIDES FOR RADIONUCLIDE-BASED RADIODETECTION AND RADIOTHERAPY

[75] Inventors: Serengulam V. Govindan, Summit; Gary L. Griffiths, Morristown; Hans L. Hansen, Mystic Island, all of N.J.

[73] Assignee: Immunomedics, Inc., Morris Plains, N.J.

[21] Appl. No.: 483,095

[22] Filed: Jun. 7, 1995

Related U.S. Application Data

[63] Continuation-in-part of Ser. No. 253,772, Jun. 3, 1994, abandoned.
[51] Int. Cl.$^6$ .......................... A61K 51/00; A61M 36/14
[52] U.S. Cl. ...................... 424/1.69; 424/1.11; 424/1.65; 530/300
[58] Field of Search .......................... 206/569; 424/1.69, 424/9.1, 1.11, 1.65; 530/300, 309, 311, 324–330; 534/10, 14, 15

[56] References Cited

U.S. PATENT DOCUMENTS

| | | | |
|---|---|---|---|
| 4,323,546 | 4/1982 | Crockford et al. | 424/1 |
| 4,424,200 | 1/1984 | Crockford et al. | 424/1.1 |
| 4,883,862 | 11/1989 | Chervu et al. | 530/331 |
| 4,932,412 | 6/1990 | Goldenberg | 128/654 |
| 5,026,913 | 6/1991 | McBride et al. | 534/10 |
| 5,061,641 | 10/1991 | Shochat et al. | 436/545 |
| 5,080,884 | 1/1992 | McBride et al. | 534/10 |
| 5,082,930 | 1/1992 | Nicolotti et al. | 530/402 |
| 5,095,111 | 3/1992 | Lever et al. | 534/14 |
| 5,102,990 | 4/1992 | Rhodes | 424/1.69 |
| 5,128,119 | 7/1992 | Griffiths | 424/1.69 |
| 5,180,816 | 1/1993 | Dean | 424/1.69 |
| 5,196,515 | 3/1993 | Lever et al. | 424/1.53 |
| 5,225,180 | 7/1993 | Dean et al. | 424/1.1 |
| 5,242,679 | 9/1993 | Fritzberg et al. | 424/1.69 |
| 5,245,018 | 9/1993 | Kondo et al. | 424/1.69 |
| 5,310,536 | 5/1994 | Srinivasan | 424/1.69 |
| 5,382,654 | 1/1995 | Lyle et al. | 534/10 |
| 5,395,946 | 3/1995 | Goedemans et al. | 549/28 |
| 5,443,815 | 8/1995 | Dean et al. | 424/1.69 |
| 5,443,816 | 8/1995 | Zamora et al. | 424/1.69 |

FOREIGN PATENT DOCUMENTS

| | | |
|---|---|---|
| 9425488 | 10/1994 | WIPO . |
| 9533495 | 12/1995 | WIPO . |

OTHER PUBLICATIONS

Greenfield, et al. "Thiol–Containing Cross–Linking Agent with Enhanced Steric Hindrance," *Bioconjugate Chem.* 1, 400–10 (1990).

Khaw et al.—J. Nucl. Med. 23:1011–19 (1982), "Technetium–99m Labeling of Antibodies to Cardiac Myosin Fab and to Human Fibrinogen".

Khaw et al.—Science, 209:295–97 (1980), "Myocardial Infarct Imaging of Antibodies to Canine Cardiac Myosin with Indium–111–Diethylenetriamine Pentaacetic Acid".

Krejcarek, et al.—Biochem. Byophys. Res. Commun., 77:581–85 (1977), "Covalent Attachment of Chelating Groups to Macromolecules".

Childs, et al.—J. Nucl. Med., 26:293 (1985), "Optimum Conditions for Labeling of DTPA Coupled Antibodies with Technetium–99m".

Fritzberg, et al.—J. Nucl. Med., 27:957, (1986), "Radiopharmaceutical Chemistry v. Antibodies".

Baidoo, et al.—Cancer Research (Supp.) 50:799s–803s, (1990), "Tc Labeling of Proteins: Initial Evaluation of a Novel Diaminedithiol Bifunctional Chelating Agent".

Wong—Chemistry of Protein Conguation and Cross–Linking, CRC Press, Inc., Boca Raton, Florida, pp. 17–23 (1991), "Reactive Groups of Proteins and Their Modifying Agents".

McCall, et al.—Bioconjugate Chem., 1:222–26 (1990), "Simplified Method for Conjugating Macrocyclic Bifunctional Chelating Agents to Antibodies via 2–Iminothiolane".

Golf, et al.—Bioconjugate Chem., 1:381–86 (1990), Substituted 2–Iminothiolanes: Reagents for the Preparation of Disulfide Cross–Linked Conjugates with Increased Stability.

Parker, Sybil P., ed., *McGraw–Hill Dictionary of Chemical Terms*, p. 211 (1984).

Virgolini, et al.—Cancer Res., 54: 690–700 (1994), "Cross–Competition between Vasoactive Intestinal Peptide and Somatostatin for Binding to Tumor Cell Membrane Receptors".

Virgolini, et al.—J. Nucl. Med., 35(5): 97P (1994), "Vasoactive Intestinal Peptide (VIP) Receptor Imaging in the Localization of Intestinal Adenocarcinomas and Endocrine Tumors".(abstract).

Maini, et al.—Nucl. Med. Commun., 14:962–968 (1993), "Somatostatin Receptor Imaging in Small Cell Lung Cancer Using $^{111}$In–DTPA–octreotide: a Preliminary Study".

Lamberts, et al.—New Eng. J. of Med., 323(18): 1246–1249 (1990), "Somatostatin–Receptor Imaging in the Localization of Endocrine Tumors".

*Primary Examiner*—John Kight
*Assistant Examiner*—Dameron Jones
*Attorney, Agent, or Firm*—Foley & Lardner

[57] ABSTRACT

A method of radiolabeling a peptide, e.g., somatostatin or an analogue thereof or vasoactive intestinal peptide, with a radioisotope of technetium or rhenium, comprises the steps of: (a) reacting the peptide with an acetyl-protected t-thiol-containing, amine-reactive bifunctional chelating agent; (b) deprotecting the acetyl-t-thiol group to generate a free t-thiol group; and either (c) admixing the peptide-t-thiol-containing conjugate with a stannous salt; and (d) reacting the mixture of step (c) with pertechnetate or perrhenate, or (c') adding reduced pertechnetate or perrhenate to said peptide-t-thiol-containing conjugate, thereby forming a radiolabeled peptide. Kits for effecting the radiolabeling method, and methods of tumor detection/imaging or therapy are provided.

30 Claims, No Drawings

THIOLATION OF PEPTIDES FOR RADIONUCLIDE-BASED RADIODETECTION AND RADIOTHERAPY

REFERENCE TO RELATED APPLICATIONS

This application is a continuation-in-part of Govindan et al., U.S. patent application Ser. No. 08/253,772, filed Jun. 3, 1994 now abandoned (hereinafter, "the '772 application"), which is incorporated herein in its entirety by reference.

BACKGROUND OF THE INVENTION

1. Field of the Invention

This invention relates to one-vial methods and kits for radiolabeling peptides with a radiometal ion of a radionuclide that binds tightly to sulfhydryl groups, wherein the peptide is derivatized with a tertiary thiol-containing chelating agent. A protected thiol-containing moiety is conjugated to the peptide, after which the derivative can be deprotected to generate free sulfhydryl groups without cleaving disulfide bonds. The derivative then can bed labeled with a radionuclide.

2. Description of Related Art

It is known that certain radiometals bind tightly to sulfur ligands, including, e.g., Tc-99 m from reduced pertechnetate, Re-186 and Re-188 ions from reduced perrhenate, Cu-67 ions, Hg-197 ions and Bi-212 ions. Some of these radiometals have been bound to proteins, especially antibodies or antibody fragments. Technetium-99 m is an ideal radionuclide for scintigraphic imaging because of its nuclear properties. Technetium-99m has a single photon energy of 140 KeV, a half-life of about 6 hours and it is readily available from a $^{99}$Mo-$^{99m}$Tc generator.

The element below technetium in the periodic table, rhenium, has similar chemical properties and can be labeled to protein using similar techniques. There are some 34 isotopes of rhenium and two of them in particular, rhenium-186 ($t_{1/2}$ 90 hours, gamma 137 KeV, beta 1.07, 0.93 MeV) and rhenium-188 ($t_{1/2}$ 17 hours, gamma 155 KeV, beta 2.12 MeV) are prime candidates for radiotherapy using targeting peptide approaches.

Direct labeling of antibodies or antibody fragments with radiometals has been successful, in large part because disulfide bonds linking heavy chains have been selectively cleaved and serve as ligand binding sites for the radiometal ions. This approach has been particularly successful with antibody fragments, especially Fab and Fab' fragments. Where a peptide to be labeled contains a disulfide group whose integrity must be preserved in order to retain the peptide's binding specific, an approach which cleaves disulfide groups is of little use.

A second method of radiolabeling proteins is indirect labeling, wherein a complexing agent (chelator) is coupled to the protein and the radiometal is bound to the protein as a chelate. Some chelators contain free or protected sulfhydryl groups that are capable of complexing with the reduced radionuclide on one end and groups capable of reacting with the peptide on the other end.

It has been discovered that receptors for certain biological peptides such as somatostatin (SS) and vasoactive intestinal peptide (VIP) are expressed at different types of tumor sites, as well as in tissues throughout the body due to normal physiological function of these peptides. Virgolini et al., Cancer Res, 54:690–700, 1994; Virgolini et al., J Nucl Med, 35:97P, 1994. Labeling small peptides such as SS and VIP therefore would be advantageous from the standpoint of tumor imaging. These small peptides and analogues thereof have been labeled with In-111 or I-123 for imaging purposes. It is known that octreotide (OCT), an octapeptide with a six amino acid disulfide loop and a diethylenetriaminepentaacetic acid (DTPA) chelator, labeled with In-111, can image small cell lung cancers by binding to SS receptors. Maini et al., Nucl Med Commun, 14:962–968, 1993. Another tyrosine analogue of the octapeptide, Tyr$^3$-octreotide (T-OCT), labeled on the tyrosine with I-123, has been shown to bind to endocrine tumors. Lamberts, et al., N Engl J Med, 323:1246–1249, 1990. Although some synthetic peptides labeled with Tc-99 m have been examined for thrombus imaging or infection imaging, Tc-99 m or rhenium labeled SS or VIP for cancer diagnosis and treatment has not received much attention.

The structures of SS, OCT, T-OCT and VIP are shown below.

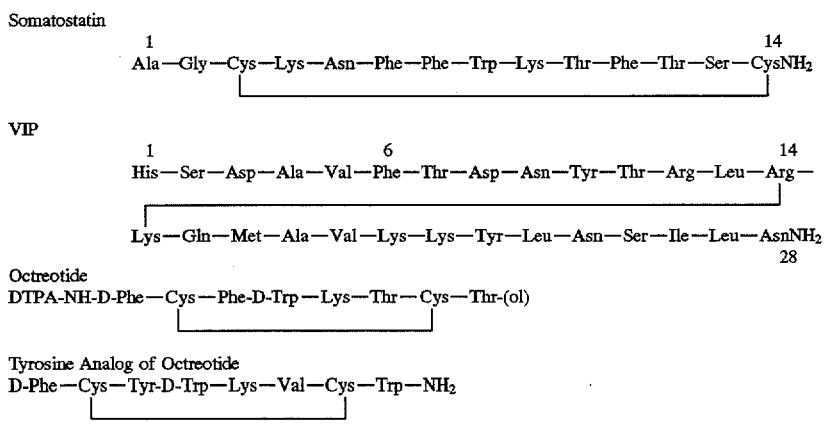

SS, OCT, T-OCT and VIP all lack a free sulfhydryl group. In order to effect efficient labeling with, e.g., Tc or Re ions from reduced pertechnetate or perrhenate, thiols must be introduced. This is complicated further by the fact that SS and its analogues contain a disulfide loop, the preservation of which is essential to maintain a conformation which binds well to its receptor. Consequently, any reaction that involves cleavage of disulfide bonds to generate thiols is excluded, and even the use or generation of thiols can cause intermolecular or intramolecular cleavage of the disulfide loop.

It also would be desirable to prolong the in vivo half-life of the labeled peptides to permit a higher percentage of the injected dose to localize at the target site.

Thus, there exists a need to develop a method of labeling small peptides such as SS and VIP using a chelator reagent (i) that is capable of reacting with a peptide that does not already contain a sulfhydryl group, and (ii) that can be transformed into a sulfhydryl—containing ligand after conjugation to the peptide, without disulfide cleavage either before or after generation of the free sulfydryl group, so that the conjugate can be combined with stannous ions and either frozen or lyophilized without disulfide cleavage, and will form a stable chelate with reduced technetium or rhenium ions upon contact with radiopertechnetate or radioperrhenate, in a one-pot labeling process. There also exists a need to develop a labeling kit for preparing radiolabeled SS and its analogues and VIP that is easy to use and does not involve complicated synthetic procedures or multiple containers for the peptide and reducing agent. There also exists a need to develop a method of radiolabeling a peptide for use in radioimaging or radiotherapy whereby the radiolabeled peptide has good tumor uptake, low kidney uptake, does not clear entirely in the liver, distributes broadly throughout the body, can be designed to have a high in vivo half life and provides a good tumor to non-tumor ratio for imaging purposes.

SUMMARY OF THE INVENTION

It is an object of the present invention to provide a method and kit useful for radiolabeling a small peptide such as somatostatin or vasoactive intestinal peptide with a radioisotope of Tc or Re, using a chelating agent that is easy to synthesize, wherein the method does not involve complicated reducing procedures including the use of excess reducing agent, and does not result in premature cleavage of the peptide during incubation with the reducing agent for the radionuclide. It also is an object of the present invention to provide a one-vial method and kit for radiolabeling the peptide with Tc or Re that is easy to use by a clinician or technician. An additional object of the present invention is to provide a method and kit for radiolabeling the peptide with Tc or Re for use in imaging or therapy, whereby the radiolabeled peptide has good tumor uptake, low kidney uptake, does not clear entirely in the liver, distributes broadly throughout the body, can be designed to have a high in vivo half life and provides a good tumor to non-tumor ratio for imaging purposes.

In accordance with these and other objects of the present invention, there is provided a method of radiolabeling a peptide with a radioisotope of technetium or rhenium, comprising the steps of:

(a) reacting a small peptide that does not contain a free sulfhydryl group, with an acetyl-protected tertiary thiol-containing bifunctional chelating agent containing an amine-reactive functional group, to form a peptide-acetyl-t-thiol-containing conjugate;

(b) deprotecting the acetyl-t-thiol group to generate a free t-thiol group; and (c) admixing the peptide-t-thiol-containing conjugate with a stannous salt for reduction of pertechnetate or perrhenate, the radionuclide to be added in a subsequent step, to form a mixture of reducing agent and peptide-t-thiol-containing conjugate; and (d) reacting the mixture of step (c) with pertechnetate or perrhenate, whereby Tc or Re cations bind to the t-thiol group, thereby forming a radiolabeled peptide, or (c') adding reduced pertechnetate or perrhenate to said peptide-t-thiol-containing conjugate, thereby forming a radiolabeled peptide.

Kits for effecting the radiolabeling method, and methods of tumor detection/imaging or therapy are provided.

DETAILED DESCRIPTION

The present inventors have found that a peptide, e.g., somatostatin (SS) or vasoactive intestinal peptide (VIP), having pendant sulfhydryl groups by virtue of the use of a chelating agent containing protected pendant thiol groups which are subsequently deprotected to generate free sulfhydryl groups, can selectively bind radiometal ions to form tight bonds to the sulfhydryl groups. These radiolabeled peptides are very effective when used in radioimaging and radiotherapeutic methods due to their ability to attach to tumor, avoid excessive kidney uptake, avoid excessive clearance to the liver, survive longer in-vivo and provide good tumor to non-tumor ratios. In addition, the method of radiolabeling enables one-pot labeling of a peptide whose disulfide bonds have not been prematurely cleaved, i.e., SS, whereby the peptide is conjugated with a chelating agent and then contacted with a reducing agent for the radionuclide in such a manner that the reducing agent does not cleave the peptide. The present inventors further have found that a peptide can be labeled in the above manner without the need to reduce the peptide thereby running the risk of cleaving disulfide bonds or altering the binding specificity or affinity of the peptide. In addition, the present inventors have found that the use of a tertiary thiol containing chelating agent allows attachment to a peptide without generating free sulfhydryl groups on the peptide or reducing the peptide, and without cleavage of the protected thiol groups on the chelating agent thereby preventing premature deprotection and oxidative loss of free thiol groups. Both the reagents and the conditions in the present method are greatly simplified, and the method is particularly suitable for technetium or rhenium labeling either utilizing a transchelator such as glucoheptonate or by using tin as a reducing agent in a one-vial kit.

Throughout this description, the term "peptide" denotes a biological (i.e., natural) or synthetic compound containing two or more amino acids linked by the carboxyl group of one amino acid and the amino group of another. Any peptide can be labeled in accordance with the present methods, but as a practical matter, those peptides that are biologically useful typically are labeled. Hence, peptides that recognize receptor sites that are expressed at various types of tumor sites and other tissues throughout the body are particularly suitable for use in the present invention. Of these peptides, SS and analogues thereof and VIP are particularly preferred.

Indirect labeling of peptide using a protected tertiary thiol-containing chelating agent to generate an acetyl-t-thiol-containing peptide derivative enables attachment to specific non-targeting binding sites on the peptide without premature cleavage of the protected thiol at the other end of the tertiary thiol-containing chelating agent and without cleavage of disulfide bonds in the peptide. This aspect of the invention is particularly important for radiolabeling SS wherein the loop structure due to a cystine disulfide bond is important in receptor binding. In addition, the present inventors have found that the disulfide bond of the peptide in the peptide-chelating agent conjugates of the present invention, when admixed with a stannous salt reducing agent for a pertechnetate or perrhenate, in a one-vial kit, is not cleaved to produce smaller fragments that may not have the requisite binding specificity or to produce pendant sulfhydryl groups on the peptide. Hence, the use of the t-thiol-containing chelating agents of the present invention enables labeling specifically on the deprotected chelating agent's pendant sulfhydryl groups and not on any free sulfhydryl groups present on the peptide that may have been inadvertently generated by reduction.

The protected tertiary thiol-containing chelating agent has an enhanced resistance to acyl cleavage reactions thereby preventing the reactive functionalities on the peptide, i.e., the amino functionalities, from prematurely deprotecting the thiol groups, and the use of the inventive chelating agents prevents inadvertent reduction of disulfide bonds in the peptide. The present method further substantially avoids the undesirable formation of colloid during the course of the labeling process and, under appropriate proportions of reducing agent and exclusion of oxygen, the present method prevents the accumulation of residual pertechnetate as a contaminant. When the t-thiol containing chelating agent further includes an unnatural amino acid, the resulting labeled peptide has a potentially increased in vivo half life due to the body's inability to recognize and attach to or react with the unnatural amino acid.

Throughout this description, the term "unnatural amino acid" denotes an amino acid that is not naturally produced by the body. Usually, these unnatural amino acids include isomers of natural amino acids or other chemical modifications of natural amino acids. For example, L-phenylalanine represents a natural amino acid that is recognized in vivo, and an example of an unnatural amino acid analog of L-phenylalanine would be D-phenylalanine. D-phenylalanine is a particularly preferred unnatural amino acid although those skilled in the art recognize that numerous other unnatural amino acids can be synthesized and utilized in the context of the present invention.

It will be understood that the peptides, including SS and VIP, to be radiolabeled can also be peptides that target antigens which include but are not limited to antigens produced by or associated with tumors, infectious lesions, microorganisms, parasites, myocardial infarctions, clots, atherosclerotic plaque, or normal organs or tissues. Advantageously, the peptides useful in radioimmunotherapy are targeting peptides that bind to cells and tissues which are associated with a disease state. Hence, by killing these cells or tissues, the disease state can be alleviated. This binding typically occurs to complementary molecules and structures associated with or expressed on the surface of the diseased cells or tissue, which preferably are not associated with or expressed on the surface of healthy cells.

More typically, the complementary moieties will be present on healthy cells, but to a lesser extent than is observed in the disease state. For example, many myelomas show large increases in expression of the interleukin 6 (IL-6) receptor compared to normal tissue. Labeled peptides targeted at the IL-6 receptor could bind preferentially to myeloma cells, leading to a high effective concentration of radiolabeled peptide and causing preferential cell killing at the site of the tumor. Another example is carcinoembryonic antigen (CEA) which is highly expressed on the surface of many tumors. A radiolabeled peptide fragment that targets CEA will cause preferential cell killing at the tumor site. It will be understood by those skilled in the art that preferential cell killing is effected by using radiometal ions that are therapeutically effective in radioimmunotherapy such as rhenium ions and the like.

The present method advantageously labels peptides such as SS, SS analogues and VIP. Analogues of SS include shorter peptides that also contain a disulfide loop and certain of the critical amino acids in SS. As noted above, these peptides have been labeled with In-111 or I-123 for imaging. These radioisotopes generally are less desirable to nuclear medicine departments than Tc-99 m. It has been found that reaction of SS, OCT, T-OCT and VIP with a protected tertiary thiol-containing chelating agent, followed by deacetylation and reaction with reduced pertechnetate, e.g., using a glucoheptonate kit, results in highly efficient labeling of the peptide.

The method of the present invention includes reacting the peptide with a protected tertiary thiol-containing chelating agent to produce a peptide-chelating agent conjugate that contains at least one protected tertiary thiol group. The tertiary thiol-containing chelating agent is covalently bound to the peptide and serves to couple the peptide and the radiometal after deprotection. Methods for effecting such covalent bonding are well known to those skilled in the art. For example, an active ester (e.g., N-hydroxysuccinimide ester) or an isothiocyanate derivative of the chelating agent may be used to bind the agent to amino functions on the peptide; a 2-iodoacetyl or maleimido derivative of the chelating agent may be used to bind the agent to sulfhydryl groups of the peptide; a hydrazide derivative of the agent may be used to bind the agent to oxidized carbohydrate groups on the peptide; or a carbodiimide reagent such as 1-ethyl-3-(3-diaminopropyl)carbodiimide may be used to bind a carboxyl group of the chelating agent to an amino group on the peptide. Advantageously, the protected tertiary thiol-containing chelating agent of the present invention contains an active ester and binds to an amine function on the peptide.

It also is useful to include an unnatural amino acid in the chelator. This has been found to prolong the in vivo half-life of the peptide-chelator conjugate. A preferred unnatural amino acid is D-phenylalanine.

The protected tertiary thiol-containing chelating agents useful in the present invention are any chelating agents containing (i) a functional group capable of forming a stable bond with a peptide functionality, as described above, and (ii) a complexing portion containing at least one protected tertiary thiol group which portion is capable of complexing a desired radionuclide after deprotection, and that does not react with the peptide functionality to prematurely deprotect the thiol group. Advantageously, the tertiary thiol-containing chelating agent forms a 5- or 6-membered ring complex with the desired radionuclide.

It is convenient for the tertiary thiol group to be part of a carboxylic acid so that it can be joined easily to the peptide or to a short linker that eventually is bound to the peptide. The '772 application discloses a chelator suitable for use in the present invention. Preferred such chelators include, but are not limited to (N-hydroxysuccinimidyl)-N-(3-methyl-3-acylmercapto butyryl) glycinate (compound I below) and reaction products of this compound with diglycine or triglycine. Alternatively, the chelating agent can include, but is not limited to D-phenylalanine derivatives of (N-hydroxysuccinimidyl)-N-(3-methyl-3-acylmercapto butyryl) glycinate and reaction products of this compound with diglycine or triglycine (Compound II below). These particularly preferred chelating agents are represented by the following formulae.

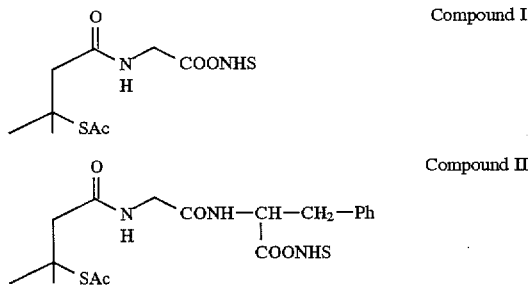

Compound I

Compound II

Pendant sulfhydryl groups present in the chelating agent may be incompatible with a sulfhydryl-selective electrophile which may be part of the same chelating agent. More importantly, where the peptide to be conjugated to the chelator also contains a disulfide bridge or loop, a free sulfhydryl group in the chelator could cleave the loop or bridge and fragment the peptide or destroy a conformation essential for binding to the receptor. In such cases, the sulfhydryl group is suitably protected during attachment of the chelating agent. The protected thiol then can be deprotected using mechanisms well known to those skilled in the art. The phrase "protected thiol" as used herein denotes a thiol-containing moiety wherein the thiol group is reversibly derivatized such that the thiol is rendered unreactive. After attachment to the peptide protein substrate, the chelating moiety can be deprotected to unmask the chelating functionality for radionuclide binding. In particular, the protected thiol is deprotected to generate pendant free sulfhydryl groups capable of complexing with the radionuclide.

Groups that are suitable for protecting the thiol from reaction are organic and inorganic groups which can readily be removed under mild conditions to regenerate the free sulfhydryl in the presence of the peptide without substantially altering the activity of the peptide. Advantageously, the thiol protecting group is an acyl group that forms a thiol ester. Preferably, the acyl group is a lower acyl group, especially an acetyl group.

Those skilled in the art are familiar with the procedures of protecting and deprotecting thiol groups and to do so within the confines of the present invention is within the purview of the ordinarily skilled artisan. A preferred method of cleaving an acyl protecting group on a tertiary thiol is reaction with hydroylamine. This is a mild reaction that normally does not affect other functional groups on a peptide and also does not cleave disulfide bonds.

Once the thiol is deprotected, a radionuclide that binds to sulfhydryl is added. In particular, reduced pertechnetate or perrhenate. As is well known in the art, radioisotopes of technetium and rhenium are conveniently supplied in the form of "generators", i.e., other radioactive precursors that decay to soluble pertechnetate or perrhenate salts that can be "milked" from the generator using saline. These reduced species are conveniently stabilized with a transchelator such as glucoheptonate and the like, many of which are available as commercial kits. The stabilized chelates of the Tc or Re salts are added to the chelator-peptide conjugate and the stronger-bonding sulfhydryl displaces the transchelator and takes up the radiometal ion.

A disadvantage of the foregoing is that it is a two-step process, where the pertechnetate or perrhenate first is added to a mixture of a reducing agent, typically a stannous ion salt, and the transchelator, in a first vial, and allowed to form a chelate of the reduced Tc or Re species. Next, the Tc or Re chelate is added to a second vial containing the peptide-chelator conjugate to effect the transchelation/labeling reaction. Losses are inevitable in transferring the Tc or Re chelates and there is a risk of spills and contamination. It would be desirable to add the generator effluent directly to a single vial for labeling.

This is accomplished according to the invention by adding to the deprotected peptide-chelating agent conjugate a reducing agent for reducing a radionuclide, where the radionuclide is to be added later. The preferred reducing agent is a stannous ion salt, e.g., stannous chloride. Reduction of disulfide bonds by stannous ions is a relatively slow reaction. The deprotected peptide-chelating agent conjugate and the reducing agent typically are frozen or lyophilized, thereby preventing cleavage of disulfide bonds in the peptide due to the presence of the reducing agent.

The present invention also encompasses a kit that includes a deprotected peptide-chelating agent conjugate and, optionally, a reducing agent for reducing a radionuclide, where the radionuclide is to be added subsequently. It is possible to use a protected tertiary thiol conjugate and add the deprotecting agent before or together with the radionuclide. The single vials or kits of the present invention are designed to contain the appropriate peptide, complexed with the tertiary thiol-containing chelating agent, for any particular immunodiagnostic or immunotherapeutic procedure.

In accordance with the present method, the vials or kits advantageously are sealed and provided with a mechanism of introducing or withdrawing reagents under sterile or semi-sterile conditions. Preferably, a vial containing a port for syringe injection is used in the present method. The reagents in the vials or kits typically are provided in aqueous, frozen or lyophilized form. In one embodiment, the reagents can be stored at low temperature, e.g., in the refrigerator or freezer or at dry ice or liquid nitrogen temperatures, for several days to several weeks, preferably at a pH of about 3.5–5.5, more preferably at pH 4.5–5.0, advantageously under an inert gas atmosphere, e.g., nitrogen or argon.

It also is within the scope of the present invention to provide the reagents in lyophilized form for ease of storage and stabilization. This is advantageously effected at pH of about 5.5, from a solution of a volatile buffer, e.g., ammonium acetate, and preferably also in the presence of a stabilizer to prevent aggregation, e.g., a sugar such as trehalose or sucrose. Such lyophilization conditions are conventional and well known to the ordinarily skilled artisan. The reagents also can be frozen and then thawed prior to use, but this procedure carries a greater risk of reoxidation and aggregation of the peptide-chelating agent conjugate.

Where the kit does not contain a reducing agent, prereduced Tc or Re cationic chelates are added to effect labeling. If stannous salts are present in the kit, it suffices to add pertechnetate or perrhenate generator effluent for in situ reduction and labeling. The contents of the vial then are mixed and incubated for a time sufficient to effect labeling of the protein. The duration and condition of incubation are not crucial, but incubation typically is carried out for a period of time sufficient to obtain substantially 100% incorporation of $^{99m}$Tc to the peptide. "Substantially 100% incorporation," as it pertains to technetium labeling, denotes greater than 98% incorporation, advantageously, greater than 99% and more advantageously 100% incorporation. Usually, the incubation is conducted for a period of time of from about 0.1 to about 60 minutes, and advantageously for a period of time of from about 1 to about 5 minutes. The radiolabeled peptide then can be withdrawn from the vial, and immediately used since separation or purification is not required.

The reducing agent for the radionuclide advantageously is tin(II), preferably in the form of stannous ions. Typically, stannous chloride is added to the mixture containing the peptide-chelating agent conjugate. It is understood by those skilled in the art that stannous ions can be generated in situ from tin metal, e.g., foil, granules, powder, turnings and the like, by contact with aqueous acid, e.g., HCl and is usually added in the form of $SnCl_2$, advantageously in a solution that is also about 0.1 mM in HCl.

In general, it is advantageous to work with a concentration of peptide of about 0.01–10 mg per ml, preferably about 0.1–5 mg/ml, of solution, generally in saline, preferably buffered to a mildly acidic pH of about 4.0–4.5. In such case, the amount of stannous ion needed for reduction of a normal imaging activity of pertechnetate is about 0.1–50 µg/ml, preferably about 0.5–25 µg/ml, in proportion to the amount of peptide. When labeling the foregoing quantity of peptide, the amount of pertechnetate generally is about 2–50 mCi/mg of peptide, and the time of reaction is about 0.1–30 minutes. With the preferred concentrations of peptide and stannous ions, the amount of pertechnetate preferably is about 5–30 mCi/mg, and the time of reaction preferably is about 1–20 minutes.

Pertechnetate is generally obtained from a commercially available generator, most commonly in the form of $NaTcO_4$, normally in saline solution. Other forms of pertechnetate may be used, with appropriate modification of the procedure, as would be suggested by the supplier of a new form of generator or as would be apparent to the ordinarily skilled artisan. Pertechnetate is generally used at an activity of about 0.2–10 mCi/ml in saline, e.g., 0.9% ("physiological") saline, buffered at a pH of about 3–7, preferably, 3.5–5.5, more preferably about 4.5–5.0. Suitable buffers include, e.g., acetate, tartrate, citrate, phosphate and the like. The reduction of pertechnetate normally is conducted under an inert gas atmosphere, e.g., nitrogen, argon or the like. The reaction temperature is generally maintained at about room temperature, e.g., 18°–25° C.

Throughout this description, the phrases "reduced pertechnetate" or "reduced perrhenate" denote the species of technetium or rhenium ion formed by stannous ion reduction of pertechnetate or perrhenate and chelated by the thiol group(s). It is generally thought that reduced pretechnetate is in the form of Tc(III) and/or Tc(IV) and/or Tc(V) in such chelates, and that reduced perrhenate is in the form of Re(III) and/or Re(IV) and/or Re(V), but higher or lower oxidation states and/or multiple oxidation states are included within the scope of the present invention.

Rhenium is found just below technetium in the periodic table, has the same outer shell electronic configuration and therefore is expected to have very similar chemical properties to technetium, especially its behavior with analogous compounds. In fact, rhenium compounds qualitatively behave similarly to technetium compounds insofar as reduction and chelation are concerned but their reaction rates are quite different and they are dissimilar in certain important respects. Despite these differences, the skilled artisan is capable of modifying the present invention based on the disclosure of technetium labeling to achieve efficient rhenium labeling (see, for example, Griffiths, U.S. Pat. No. 5,128,119, the disclosure of which is incorporated by reference herein in its entirety).

The radioisotope Re-186 is attractive for therapy and can also be used for imaging. It has a half-life of about 3.7 days, a high LET beta emission (1.07) MeV) and a convenient gamma emission energy (0.137 MeV). By analogy to technetium, rhenium is produced from perrhenate, and the reduced rhenium ions can bind non-specifically to peptide. Accordingly, a method for Re-186 labeling of peptides, wherein the reduced perrhenate is bound to sulfhydryl groups on a peptide-chelating agent complex, would be advantageous. Re-188 is a generator-produced beta and gamma emitter with a half-life of about 17 hours and is suitable for imaging and therapy. The development of commercial generators for rhenium-188 is currently underway; and in a preferred scenario, carrier free rhenium-188 is added directly to a vial containing stannous ions and a peptide-chelating agent complex, to produce a rhenium radiolabeled peptide which is ready for use in less than about two hours.

In general, the concentration of uncomplexed peptide, e.g., SS or VIP, the reaction times, perrhenate activities and other conditions will be substantially the same as for Re-186 or Re-188 labeling, except that a larger amount of stannous ion is used. When the radioisotope in the radioperrhenate is substantially carrier-free Re-188, the concentration of peptide in the solution is advantageously about 1–20 mg/ml, preferably about 10–20 mg/ml and the amount of stannous ion is about 500–10,000 µg/ml, preferably about 500–5,000 µg/ml. When the radioisotope in the radioperrhenate is carrier-added Re-186, at the same concentration of antibody or antibody fragment, the amount of stannous ion is about 5–1,000 mg/ml, preferably about 50–500 mg/ml.

Copper ions also are tightly chelated by sulfur chelators. Cu-67 is another attractive radionuclide for imaging and therapy. It has a half-life of about 2.6 days, a beta emission (0.57 MeV) and a gamma emission (0.185 MeV), although the beta energy is relatively low. Cu-67 is relatively expensive and not readily available at present, although such conditions may change as demand develops. Cu-67 has the advantage that if forms tight chelates with thiols, the labeling is simple and rapid, and requires no reducing agent for the radiometal.

Other radionuclides with similar chelation behavior to copper, e.g., mercury, silver and lead, also could be bound to thiol-containing compounds according to the method of the present invention. Hg-197 has a half-life of about 1.5 days, and emits gamma radiation in an energy range of 78–268 KeV, and Pb-203 is a strong gamma-emitter at about 275 KeV, with a half-life of about 51 hours, making mercury and lead suitable for gamma scintigraphy. Ag-111 has a half-life of 7 days and emits beta radiation at about 1.02 MeV, and Bi-212 is an alpha-emitter with a half-life of about 1 hour and an energy of 6.09 MeV, making them of considerable interest for in vivo therapy. Bi-212 is produced in situ from a Pb-212 precursor with emission of gamma radiation of 239 KeV, with a half-life of about 10.6 hours. Thus, peptide-tertiary thiol-containing chelating agent conjugates for Bi-212 therapy will be Pb-212-labeled conjugates, and the short-hand notation lead/bismuth or Pb/Bi is used herein to indicate this. It will be understood that the invention is not limited to the exemplified radionuclide, but is generally applicable to ions that bind tightly to sulfhydryl groups.

The aforementioned labeling conditions typically result in substantially 100% incorporation, or substantially quantitative incorporation, of the label into the peptide-chelating agent complex. Throughout this description, the phrase "substantial quantitative incorporation" as it pertains to rhenium labeling, denotes greater than about 80% incorporation, advantageously, greater than about 85% and more advantageously, greater than about 90% incorporation. For example, it now is possible to consistently label peptide, complexed with a tertiary thiol-containing chelating agent, with from 5 to 200 micrograms of Sn(II) per milligram of peptide, in essentially quantitative yield. Furthermore, the immunoreactivity of this labeled peptide is hardly reduced after this serum incubation, showing that the radiolabeled peptide-chelating agent conjugates are still completely viable imaging agents out to at least 24 hours.

At the aforementioned reaction conditions, for technetium labeling, no transchelator such as phosphonate, tartrate, glucoheptonate or other well known Sn(II) chelating agent is required to keep the tin in solution, however, such transchelators can be used in accordance with the present invention. Sn(II) compounds such as stannous chloride are preferred for use in the present method, although other readily available and conventional Sn(II) salts also are effective. There are only three essential ingredients; the deprotected peptide-chelating agent conjugate, the aqueous stannous ion and the pertechnetate solution. Under the reaction conditions described herein, substantially 100% of Tc-99 m incorporation into peptide can readily be achieved.

The resultant radiolabeled peptide is suitable for use in scintigraphic imaging of, e.g., tumors, infectious lesions, microorganisms, clots, myocardial infarctions, atherosclerotic plaque, or normal organs and tissues. Such imaging methods are well known in the art. The radiolabeled peptide solutions as prepared above are ready for immediate injection, if reacted in a properly sterilized, pyrogen-free vial. Also, no blocking of free sulfhydryl groups after technetium binding is necessary for stabilization.

The resultant preferred peptide-chelating agent-radiometal ion conjugate of the present invention is represented by the following formula I

[PEPTIDE]–X$_n$–[I]–M       Formula I where:

n is zero or 1;

X represents an unnatural amino acid such as D-phenylalanine;

I represents the chelating agent represented by Compound I, where the protected thiol group has been deprotected; and M represents a radiometal ion such as reduced technetium-99 m.

Preferably, the peptide is attached to X (or directly to I when n is zero) via the amino group at the N-terminus of the peptide, although attachment via the free amine group of lysine or arginine residues in the body of the peptide also is included within the context of the present invention.

Reaction Scheme I

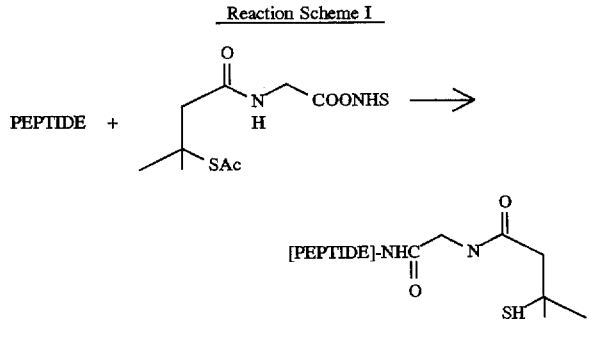

Reaction Scheme II

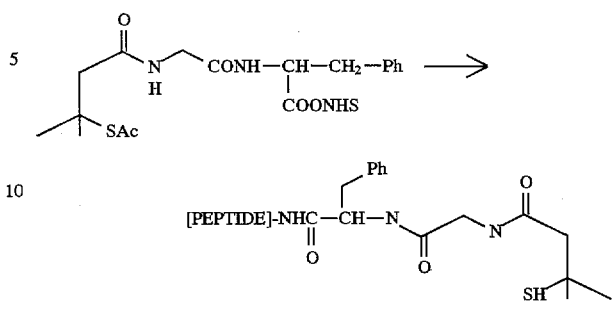

The general scheme for radiolabeling a peptide such as SS, OCT, T-OCT or VIP usually entails first reacting the peptide with the chelating agent: I in the case of using compound I, or X-I in the case of using compound II. The protected thiol group then is deprotected and the resulting peptide-deprotected chelating agent conjugate is incubated with a radiometal ion such as technetium. Synthesizing the peptide-deprotected chelating agent conjugate in accordance with the present invention can be carried out in accordance with reaction scheme I (for Compound I) and reaction scheme II (for Compound II) outlined above. More detail is provided in the '772 application.

The method of the present invention is particularly attractive for labeling SS OCT, T-OCT and VIP, although peptides that function as drugs, cytokines, enzymes, hormones, immune modulators, receptor peptides and the like may also be labeled. Peptides can contain one or more disulfide bonds which form bridges or loops within the peptide structure. Known methods that involve cleavage of these disulfide bonds typically set out to selectively cleave only the disulfide bonds that do not play a significant role in receptor binding. Unfortunately, these methods sometimes, if not carried out with caution, can cause undesirable cleavage of the disulfide bonds that do play a significant role in receptor binding thereby rendering the peptide essentially useless. In addition, use of chelating agents that have free thiol groups also can result in similar undesirable cleavage of disulfide bonds in the peptide. The present method specifically avoids such undesirable cleavage by using the protected tertiary thiol-containing chelating agent or a protected tertiary thiol-containing chelating agent containing an unnatural amino acid, and complexing the chelating agent with a functional group on the peptide, preferably an amino group thereby leaving the disulfide bonds of the peptide intact.

The method of the present invention also encompasses the use of a water-soluble transfer ligand that complexes with the reduced radionuclide. In general, the transfer ligands useful in an alternative embodiment of the present invention are water soluble (or can be made water soluble) chelators that are capable of complexing technetium-99 m or any of the rhenium radioisotopes in the reduced state or other known radioisotopes to form a stable metal ion/ligand complex. The complex further is capable of exchanging the radioisotope with the pendant sulfhydryl groups present on the peptide-chelating agent conjugate, after deprotection of the thiol group(s). Examples of suitable transfer ligands include glucoheptonate, tartrate, DTPA, EDTA, di, tri or poly-alkylphosphonates, pyrophosphate or glycine and its derivatives. Those skilled in the art recognize that any chelating agent capable of complexing with reduced radionuclide and subsequently transferring the reduced radionuclide to pendant sulfhydryl groups are useful in accordance with the present invention (see, for example, Dean, U.S. Pat. No. 5,180,816 and/or Shochat et al., U.S. Pat. No. 5,061,641, the disclosures of each are incorporated by reference herein in their entirety).

The present invention also encompasses an alternative embodiment whereby the thiol-bound radiometal is "capped" with one or more exogenous ligands (see, Shochat et al., supra). These ligands generally are designed to complete the coordination sphere of the ion and to complement the sulfhydryl group(s) already provided by the peptide-chelating agent conjugate. A balance must be struck between ligands that bind the ion so tightly that they weaken the sulfur-metal bond(s) to the peptide reactive group(s) and reduce the stability of the radiometal label in serum, and those that provide insufficient chelating power so that the ion is easily extracted from the peptide by other exogenous ligands in serum or bone marrow, or in organs such as the liver, spleen or kidneys where clearance occurs. Those skilled in the art are capable of striking this balance using known chemical principles, and are capable of designing a suitable exogenous capping ligand.

A kit for use in radiolabeling a peptide, e.g., SS, OCT, T-OCT or VIP, with Tc-99 m, using generator produced pertechnetate, would include about 0.01–10 mg per unit dose of a peptide that specifically targets an antigen associated with a tumor, an infectious lesion, a microorganism, a myocardial infarction, a clot, atherosclerotic plaque or a normal organ or tissue, and which further is conjugated to a protected tertiary thiol-containing chelating agent to form a protected peptide-acetyl-t-thiol derivative that is deprotected to form a peptide-t-thiol derivative. Alternatively, the chelating agent can include an unnatural amino acid such as D-phenylalanine or the like. The kit also would include about 0.1–50 µg per unit dose of stannous ions. The constituents of the kit are combined just prior to use with about 2–50 mCi of Tc-99 m pertechnetate per mg of peptide. The peptide-thiol derivative and the Sn(II) reducing agent are advantageously combined in a single solution in a vial which can be stored, e.g., in a liquid nitrogen bath, or lyophilized, preferably with added sugar as is well known in the art, prior to addition of the pertechnetate. Variations including addition of conventional reagents of the foregoing kits are well within the routine skill of those skilled in the art.

If the peptide-acetyl-t-thiol derivative is used, it can be deprotected prior to admixture with the reducing agent, or after admixture. The protected peptide-acetyl-t-thiol derivative, however, should be deprotected prior to reaction with the radionuclide. Although the deprotecting agent and the radionuclide may be added to the solution simultaneously, the reaction sequence generally is (i) deprotection of the protected peptide-acetyl-t-thiol derivative and reduction of the radionuclide, and (ii) labeling the conjugate. Advantageously, however, the peptide-acetyl-t-thiol derivative is deprotected before admixture with the reducing agent and storage in a kit. Upon reading the present specification, those skilled in the art are capable of designing a method and kit using either a protected or deprotected peptide-acetyl-t-thiol derivative.

The peptides in the kits of the present invention are advantageously frozen or lyophilized, in sterile containers, and under an inert gas atmosphere, advantageously cooled and stored in a liquid nitrogen bath and gently thawed just prior to use. The kits are conveniently supplemented with sterile vials of buffers, saline, syringes, filters, columns and the like auxiliaries to facilitate preparation of injectable preparations ready for use by the clinician or technician.

In a particularly preferred embodiment of the present invention, radiolabeling of a peptide is effected by conjugating (N-hydroxysuccinimidyl) N-(3-methyl-3-acylmercapto butyryl) glycinate ("chelating agent") to SS OCT, T-OCT or VIP by reaction of peptide with at least a molar equivalent and more preferably, a molar excess of chelating agent at ambient temperatures and at pH within the range of about 7.0 to about 8.0. The number of thiols added to the peptides can be altered by varying the molar excess of chelating agent employed. The peptide-chelating agent conjugate then preferably is purified by conventional means (i.e., reverse-phase HPLC) and the purified conjugate can be thiol-deprotected as and when necessary, and once thiol-deprotected, the resultant product is immediately formulated with stannous chloride, and stored as a kit as a lyophilizate, in sealed vials, under an argon atmosphere or in vacuo. This kit then is ready for admixture with the radionuclide.

It will be apparent to one of ordinary skill in the art that the radiolabeled peptides, especially SS, OCT, T-OCT and VIP, prepared according to the method of the invention, will be suitable, and in fact particularly convenient and efficacious, in methods of non-invasive scintigraphic imaging and for radiotherapy of tumors and lesions. In particular, a method of imaging a tumor, an infectious lesion, a myocardial infarction, a clot, atherosclerotic plaque, or a normal organ or tissue, wherein a peptide that specifically targets to an antigen produced by or associated with the tumor, etc;, and radiolabeled with a pharmaceutically inert radioisotope capable of external detection, is parenterally injected into a human patient and, after a sufficient time for the radiolabeled peptide to localize and for non-target background to clear, the site or sites of accretion of the radiolabeled peptide are detected by an external imaging camera, it will be an improvement to use as the radiolabeled peptide a labeled peptide made according to the method of the present invention. Such radiolabeled peptide will not clear significantly in the liver, will provide a good tumor to non-tumor ratio and will provide excellent in vivo targeting to tumor.

Another important application will be for direct detection of tumor margins in intra-operative, intravascular or endoscopic examination and surgery. The radiolabeled small peptide can be used alone or in combination with a radiolabeled antibody or antibody fragment, as described, e.g., in U.S. Pat. No. 4,932,412.

In addition, in a method of radiotherapy of a patient suffering from a tumor or an infectious lesion, wherein a peptide that specifically targets an antigen produced by or associated with a tumor or an infectious lesion, and radiolabeled with a therapeutically effective radioisotope, is parenterally injected into a human patient suffering from such tumor or infectious lesion, it will represent an improvement to use as the radiolabeled peptide a rhenium radiolabeled peptide made according to the method of the present invention.

Without further elaboration, it is believed that one skilled in the art can, using the preceding description, utilize the present invention to its fullest extent. The foregoing preferred specific embodiments are, therefore, to be construed as merely illustrative, and not limitative of the disclosure in any way whatsoever. In addition, all of the previously mentioned documents in this description are incorporated by reference herein in their entirety. While the invention has been described by reference to the above particularly preferred embodiments, those skilled in the art recognize that various modifications can be made to the present invention without significantly departing from the spirit and scope thereof.

What is claimed is:

1. A method of radiolabeling a peptide with a radioisotope of technetium or rhenium, comprising the steps of:

15

(a) reacting a peptide that does not contain a free sulfhydryl group, with an acetyl-protected tertiary thiol-containing bifunctional chelating agent containing an amine-reactive functional group, to form a peptide-acetyl-t-thiol-containing conjugate;

(b) deprotecting the acetyl-t-thiol group to generate a free t-thiol group; and (c) admixing the peptide-t-thiol-containing conjugate with a stannous salt for reduction of pertechnetate or perrhenate, the radionuclide to be added in a subsequent step, to form a mixture of reducing agent and peptide-t-thiol-containing conjugate; and (d) reacting the mixture of step (c) with pertechnetate or perrhenate, whereby Tc or Re cations bind to the t-thiol group, thereby forming a radiolabeled peptide, or (c') adding reduced pertechnetate or perrhenate to said peptide-t-thiol-containing conjugate, thereby forming a radiolabeled peptide.

2. The method of claim 1, wherein deprotection step (b) is effected with hydroxylamine.

3. The method of claim 1, wherein said acetyl-protected tertiary thiol-containing bifunctional chelating agent is N-hydroxysuccinimidyl N-(3-methyl-3-acylmercaptobutyryl)-glycinate.

4. The method of claim 3, wherein said acetyl-protected tertiary thiol-containing agent is an N-hydroxysuccinimidyl ester of the N-(3-methyl-3-acylmercaptobutyryl)glycyl amide of an unnatural amino acid.

5. The method of claim 4, wherein said unnatural amino acid is D-phenylalanine, and said acetyl-protected tertiary thiol-containing bifunctional chelating agent is N-hydroxysuccinimidyl N-(3-methyl-3-acylmercaptobutyryl) glyclphenylalaninate.

6. The method of claim 1, wherein said peptide is somatostatin or an analogue thereof.

7. The method of claim 1, wherein said peptide is vasoactive intestinal peptide.

8. The method of claim 1, wherein said radionuclide is Tc-99 m.

9. The method of claim 1, wherein said radionuclide is Re-186.

10. The method of claim 1, wherein said radionuclide is Re-188.

11. A radiolabeled peptide labeled by the method according to claim 8.

12. A radiolabeled peptide labeled by the method according to claim 9.

13. A radiolabeled peptide labeled by the method according to claim 10.

14. A kit suitable for forming a technetium-radiolabeled peptide to be administered to a human patient, which comprises a sterile container containing a diagnostically effective amount of a peptide-t-thiol-containing conjugate prepared according to steps (a) and (b) of claim 1, reduced radiopertechnetate to be added in a subsequent step.

15. The kit of claim 14, wherein the contents of said sterile container are lyophilized.

16. The kit of claim 14, wherein said peptide is somatostatin or an analogue thereof or vasoactive intestinal peptide.

17. A kit suitable for forming a technetium-radiolabeled peptide to be administered to a human patient, which comprises a sterile container containing a diagnostically effective amount of a peptide-t-thiol-containing conjugate prepared according to steps (a)–(c) of claim 1, and (ii) an amount, sufficient to substantially completely reduce added radiopertechnetate, of a stannous salt, said radiopertechnetate to be added in a subsequent step.

18. The kit of claim 17, wherein the contents of said sterile container are lyophilized.

19. The kit of claim 17, wherein said peptide is somatostatin or an analogue thereof or vasoactive intestinal peptide.

20. A method of tumor detection or imaging, comprising the steps of:

(a) parenterally injecting a patient having a tumor that expresses receptors for somatostatin or vasoactive intestinal peptide with a diagnostically effective amount of Tc-99 m-labeled somatostatin or an analogue thereof or vasoactive intestinal peptide which has been radiolabeled according to the method of claim 1; and (b) detecting or imaging said tumor using a gamma detector or camera.

21. The method of tumor detection of claim 20, wherein said detection is effected directly, in an intraoperative, endoscopic or intravascular procedure, using a gamma detector.

22. The method of tumor imaging of claim 20, wherein said imaging is effected using an external gamma camera.

23. A kit suitable for forming a rhenium-radiolabeled peptide to be administered to a human patient, which comprises a sterile container containing a therapeutically effective amount of a peptide-t-thiol-containing conjugate prepared according to steps (a) and (b) of claim 1, reduced radioperrhenate to be added in a subsequent step.

24. The kit of claim 23, wherein the contents of said sterile container are lyophilized.

25. The kit of claim 23, wherein said peptide is somatostatin or an analogue thereof or vasoactive intestinal peptide.

26. A kit suitable for forming a rhenium-radiolabeled peptide to be administered to a human patient, which comprises a sterile container containing a therapeutically effective amount of a peptide-t-thiol-containing conjugate prepared according to steps (a)–(c) of claim 1, and (ii) an amount, sufficient to substantially completely reduce added radioperrhenate, of a stannous salt, said radioperrhenate to be added in a subsequent step.

27. The kit of claim 26, wherein the contents of said sterile container are lyophilized.

28. The kit of claim 26, wherein said peptide is somatostatin or an analogue thereof or vasoactive intestinal peptide.

29. A method of tumor therapy, comprising the steps of:

(a) parenterally injecting a patient having a tumor that expresses receptors for somatostatin or vasoactive intestinal peptide with a therapeutically effective amount of Re-186-labeled or Re-188-labeled somatostatin or an analogue thereof or vasoactive intestinal peptide which has been radiolabeled according to the method of claim 1.

30. The method of claim 1, wherein said peptide is from 2 to 28 amino acid residues in length.

* * * * *